United States Patent [19]

Bruno

[11] 4,383,530
[45] May 17, 1983

[54] HYPODERMIC NEEDLE AND METHOD OF MAKING NEEDLES

[76] Inventor: John Bruno, 77-83 Second Ave., Paterson, N.J. 07524

[21] Appl. No.: 270,871

[22] Filed: Jun. 5, 1981

[51] Int. Cl.³ ............................................. A61M 5/00
[52] U.S. Cl. .................................................... 604/274
[58] Field of Search ................. 128/218 N, 221, 214.4

[56] References Cited

U.S. PATENT DOCUMENTS

| | | | |
|---|---|---|---|
| 1,125,887 | 1/1915 | Schimmel | 128/221 |
| 1,569,174 | 1/1926 | Crowther | 128/221 |
| 2,697,438 | 12/1954 | Hickey | 128/221 |
| 2,748,769 | 6/1956 | Huber | 128/221 |
| 3,099,988 | 8/1963 | Ginsburg | 128/221 |
| 3,703,174 | 11/1972 | Smith | 128/214.4 |

FOREIGN PATENT DOCUMENTS 486146 11/1953 Italy ..................................... 128/221

*Primary Examiner*—John D. Yasko
*Attorney, Agent, or Firm*—Morgan, Finnegan, Pine, Foley & Lee

[57] ABSTRACT

A needle structure for hypodermic needles and the like, and method of making a needle, includes forming the beveled, sharply pointed free end of a thin, hollow needle tube so that the leading tip at the beveled end shields, at least partially, the hollow central portion of the needle tube. Advantageously, a portion of the needle tube behind the needle point diverges relatively slightly from the remainder of the needle tube so as to orient the leading tip at a slight angle with respect to the remainder of the needle tube such that it covers at least a portion of the hollow needle tube. As preferably embodied, the divergent portion is formed as a slightly arcuate segment in the needle tube ust behind the needle point, which can resemble a bulge-like formation in the needle tube. Alternatively, the needle tube can be formed with a single bend to lower the point of the needle leading tip. In a particularly useful embodiment, the present invention can be a relatively large diameter (e.g., about 0.045") needle for use in coronary assist procedures, with a helio coid conductor wire already located within the hollow needle tube.

11 Claims, 8 Drawing Figures

HYPODERMIC NEEDLE AND METHOD OF MAKING NEEDLES

BACKGROUND OF THE INVENTION

The present invention relates generally to hollow needles, and, more particularly, to the needle portion of hypodermic needles and the like for penetrating various tissues to inject drugs, medicine, etc., to implant conductor wires or other similar structures or to carry out any other appropriate biomedical function.

It is, of course, well known that great progress continues to be made in the medical sciences. New drugs are constantly being developed to treat or cure diseases, and medical problems once thought to be incurable are now routinely treated. Moreover, surgical techniques have reached such a high level of advancement and sophistication that there almost seems to be no limit to the type of tissue repair which can be achieved.

However, in all the years of progress in medicine, there has been virtually no change in one of the principal tools of the medical profession—the hypodermic needle. Basically, the hypodermic needle includes a relatively thin, straight, hollow tube coupled at one end to a syringe of one type or another. The other end is formed with a bevel of about 17° to form a sharp point, with the leading tip of the needle point being along the longest side of the needle tube.

The hypodermic needle has always performed its function of injecting drugs, medication or the like into the desired subcutaneous tissue. However, there is one universally recognized drawback to the hypodermic needle as it is currently constructed. A certain degree of trauma is suffered by the tissue(s) penetrated by the needle, due to tissue coring and/or shaving.

Thus, in conventional needles with the usual beveled tip, the coring effect results in a plug-like piece of tissue being cut-out and becoming wedged inside the needle tube. In addition, the shaving effect caused by the sharp recessed edge of the needle point (sometimes called the heel of the bevel) results in thin slices of tissue being cut during penetration and becoming lodged in the needle tube. For needles of very small tube diameter, the trauma often causes only a little discomfort, usually in the form of a dull pain which lasts a day or so after the injection. However, the larger the needle size, the greater the trauma, particularly that resulting from coring.

The tissue core and shavings will be ejected from the needle tube when fluid is released from the syringe, so they do not usually interfere with the fluid injection. However, it has recently been suspected that as these discharged tissue particles decompose, particularly when injected into the blood stream, there is a risk of developing certain types of cancer.

One design for eliminating the tissue coring and shaving effects, particularly in larger needles, involves placing a sharply pointed rod (often called an obturator) inside the needle tube with the sharp end of the obturator projecting beyond the tip of the needle (which need not, therefore, be beveled to form a sharp point). The obturator fairly well blocks the hollow needle tube during penetration by the needle, and is removed once the needle tip is at the desired depth in the tissue. However, this arrangement entails the extra expense of fabricating the obturator to fit the needle tube. Furthermore, in use, it necessarily involves the additional steps of removing the rod and safely coupling the syringe to the needle tube, and, when used in coronary assist procedures, inserting a pacer wire (i.e., a helio coid) or other conductor wire through the needle tube. In emergency or critical procedures, the time lost by performing these additional steps could be critical.

Accordingly, it is an object of the present invention to provide new and improved needle structures for hypodermic needles and the like and methods for making a needle. It is another object of the invention to provide new and improved needle structures for hypodermic needles and the like, and methods for making a needle, which is capable of easier penetration into a patient's tissue with minimum trauma.

It is also an object of the invention to provide new and improved needle structures for hypodermic needles and the like, and methods for making a needle, which substantially reduces and can virtually eliminate the coring and shaving effects experienced with conventional hypodermic needle constructions. Furthermore, the present invention is intended to be capable of embodiment in virtually any size needle for uses ranging from routine injections to precision injection/implantations such as in coronary assist procedures. In addition, the needle of the present invention can be embodied in otherwise conventional needle structures.

Objects and advantages of the invention are set forth in part herein and in part will be appreciated herefrom. However, these and other objects and advantages of the invention may be learned through practice with the invention, the same being realized by means of the structures, instrumentalities, steps, methods and combinations disclosed and claimed herein. The invention thus resides in the novel constructions, arrangements, steps, operations, combinations and improvements herein shown and described.

SUMMARY OF THE INVENTION

Briefly described, a needle structure for hypodermic needles and the like, and method of making a needle, according to the present invention includes forming the beveled, sharply pointed free end of a thin, hollow needle tube so that the leading tip at the beveled end shields, at least partially, the hollow central portion of the needle tube. Advantageously, a portion of the needle tube behind the needle point diverges relatively slightly from the remainder of the needle tube so as to orient the leading tip at a slight angle with respect to the remainder of the needle tube such that it covers at least a portion of the hollow needle tube. As preferably embodied, the divergent portion is formed as a slightly arcuate segment in the needle tube just behind the needle point, which can resemble a symmetrical bulge-like formation in the needle tube. Alternatively, the divergent portion can be a relatively small single bend in the needle tube. In a particularly useful embodiment, the present invention can be a relatively large diameter (e.g., about 0.045") needle for use in coronary assist procedures, with a helio coid conductor wire already located within the hollow needle tube during penetration.

It will be apparent from the foregoing general description that the objects and advantages of the invention specifically enumerated herein are achieved by the invention as herein disclosed. Thus, for example, by forming the needle so that the leading tip at the needle point shields at least a portion of the hollow needle tube, it will be found that the phenomenon of tissue coring during penetration of the needle is substantially reduced, and even eliminated depending on the relative angular inclination of the tip, thereby causing negligible trauma during injections with even the largest diameter needles. In addition, the shaving of tissue during penetration is equally reduced or eliminated in needles formed in accordance with the present invention, because less tissue is exposed to the sharp edge at the heel.

It will also be found that by forming a divergent portion behind the needle point, the present invention can be embodied in an otherwise conventional needle structure. Moreover, by forming the divergent portion as a curved segment behind the needle point, it will be found that the reduction or elimination of trauma is achieved without any appreciable loss of strength of the needle or risk of needle fragmentation.

Furthermore, needles fabricated in accordance with the present invention can be made on conventional equipment, without any significant increase in manufacturing costs.

It will be understood by those skilled in the art that the foregoing general description and the following detailed description are exemplary and explanatory of the invention and are not intended to be restrictive thereof. Accordingly, the accompanying drawings illustrate preferred embodiments of the invention and, together with the following detailed description, serve to explain the principles of the invention.

DETAILED DESCRIPTION OF PREFERRED EMBODIMENTS

Figure 1A:
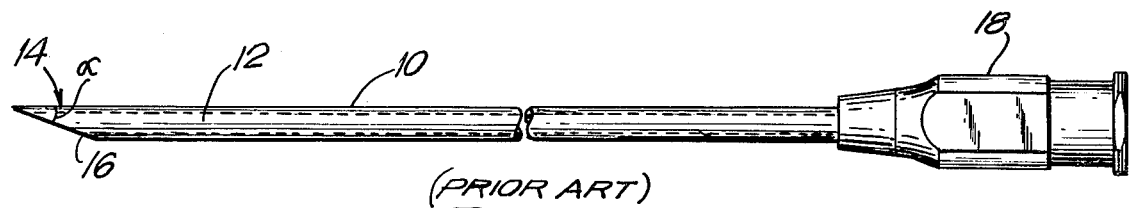
FIGS. 1A and 1B are illustrations of the current configuration for the needle portion of conventional hypodermic needle assemblies, showing the coring/shaving phenomenon when penetrating tissue (FIG. 1B).
Figure 1B:
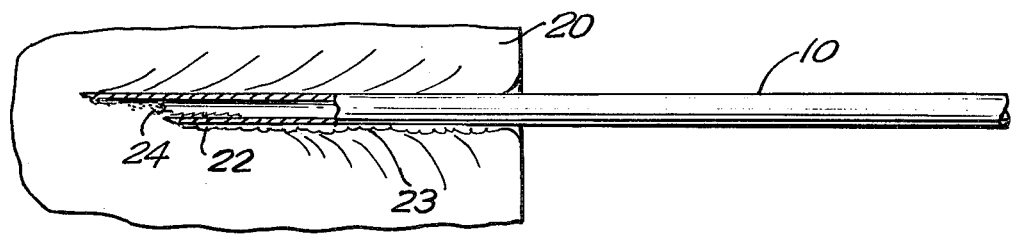
Figure 5A:
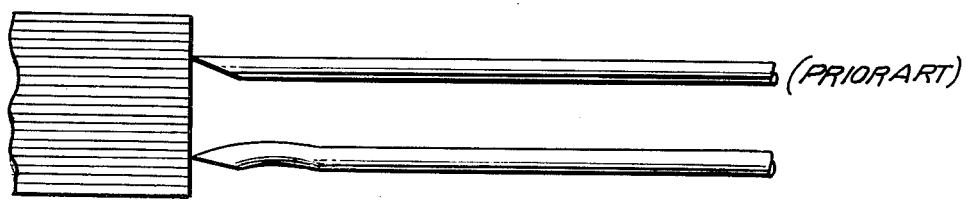
FIGS. 5A, 5B and 5C are side views showing, in sequence, a comparison of penetration of a conventional needle (the "PRIOR ART NEEDLE") and a needle made in accordance with the present invention.
Figure 5B:
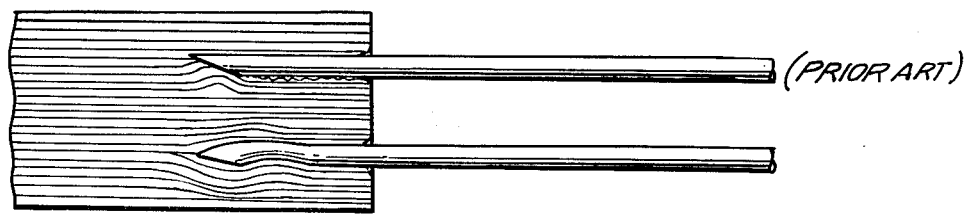
Figure 5C:
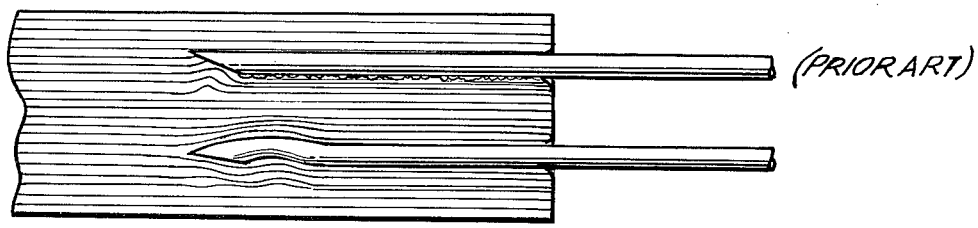

Referring first to FIGS. 1A and 1B and, in part, to FIGS. 5A thru 5C, there are shown various illustrations of a conventional configuration for the needle portion of a hypodermic needle assembly. A relatively thin, hollow needle tube 10 (with a hollow interior indicated at 12) is beveled at one end to form a sharp point at the leading tip 14, with a sharp edge 16 at the heel of the bevel. The other end of needle tube 10 is attached by conventional means to a hub 18 which either can form part of or be adapted for attachment to a syringe or like member (not shown).

Although the point of needle 10 is shown to have a straight bevel, some needle points are formed with a slightly concavely shaped bevel. In either event, the angle (indicated by $\alpha$) formed at the leading tip is generally about 17° in order to ensure sufficient structural strength in the needle tip to prevent fragmentation of the tip. It will be understood that as the bevel angle at the leading tip is reduced below 17°, the risk of fragmentation increases, unless resort is made to very expensive high strength materials.

Since the tissue cutting is done primarily by the beveled edge portions of the needle tip (the smooth cylindrical side of the needle essentially glides through the tissue), the effective needle point angle to which the tissue is exposed is the same as the angle of beveling. Thus, it is desirable to reduce the angle of the needle point to reduce the trauma, but conventional needles are limited in this regard because of the increased risk of needle fragmentation.

FIGS. 1B and 5A through 5C illustrate the trauma caused to tissue 20 during penetration of conventional hypodermic needles. Regardless of the size of the needle, there is always a certain amount of tissue shaved (as indicated at 22) by the heel (or recessed needle edge) 16 of the needle. The tissue shaving results because the heel edge 16 is necessarily sharpened to virtually the same degree as the needle point when the needle point is machined to form the beveled tip. The sharp edge thus shaves off thin slices of tissue (indicated at 22) during penetration and also leaves behind a jagged path (indicated at 23) in the tissue.

Another problem with conventional needles, particularly larger diameter needles, is the coring effect. Since the tissue penetrated by the needle is directly exposed to the open hollow center of the needle tube, a core or plug-like piece of tissue (indicated at 24) will become embedded in the needle tube, resulting in significant trauma. Coring is most serious in coronary assist procedures, because part of the heart tissue is actually removed, leaving a hole in the heart which could result in serious internal bleeding.

Figure 2:
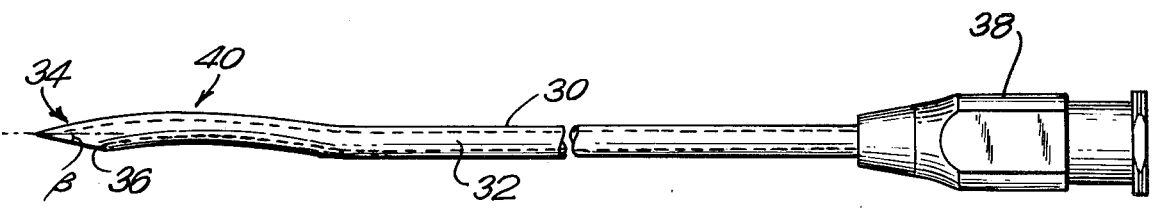
FIG. 2 is a view, from the side, of a needle member for hypodermic needles and the like made in accordance with the present invention.
Figure 3:
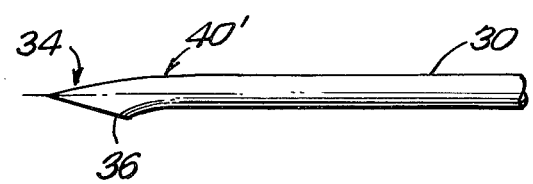
FIG. 3 is a view, from the side, of part of a modified embodiment of a needle made in accordance with the present invention.
Figure 4:
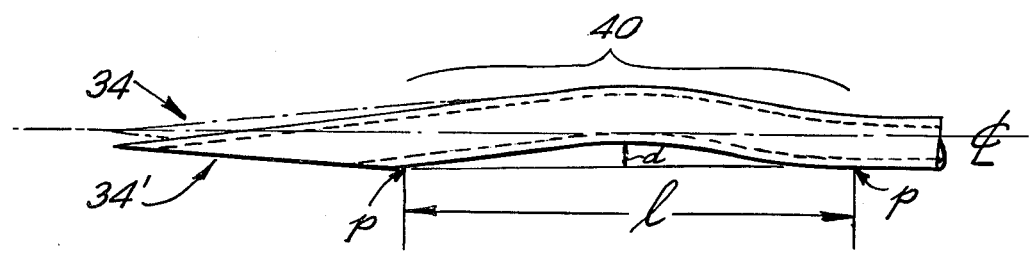
FIG. 4 is a view, from the side, of part of a needle made in accordance with the present invention, showing alternate angular configurations for the needle tip.

Turning then to FIGS. 2–4, there are shown various embodiments of the improved needle construction according to the present invention for hypodermic needles and the like. As shown in FIG. 2, the needle according to the invention is virtually identical to conventional needle in every aspect except as explained below. Thus, as an advantage achieved by the invention, the needle can be made of the same materials, and it has a thin, hollow needle tube 30 (with interior hollow portion 32), with its leading tip 34 beveled to form a sharp point and a recessed heel edge 36. It may also be attached to a hub 38 similar to hub 18 described above with respect to FIGS. 1A and 1B.

According to the invention, a portion of the needle behind the point is formed so that the outer cylindrical-like portion of leading tip 34 forms a relatively small angle with respect to the remainder of that side of the needle tube. As a result, there is a reduction in the effective cutting angle (i.e., the angle $\beta$ in FIG. 2) to which the tissue is exposed during penetration of the needle. In addition, and of high significance, the leading tip shields at least a portion of the cross-sectional area of hollow tube chamber 32, if not the entire area of interior chamber 32, so that the coring effect of conventional needles is significantly reduced or completely eliminated. Furthermore, the inclined leading tip also acts to shield tissue from the sharp heel edge 36 so that the tissue shaving and the jagged tissue path is likewise greatly reduced or eliminated. Thus, the trauma caused by penetration of the needle is virtually eliminated or at least significantly reduced, even for the largest diameter hypodermic needles.

As embodied in FIGS. 2 and 4, the shielding configuration of the leading tip is provided by forming a divergent portion 40 in the needle tube behind the needle point. The divergent portion is proportioned so as to terminate at or very near the leading tip of the needle and thereby orient the leading tip at the desired angular inclination. As shown in FIGS. 2 and 4, both ends of the divergent portion are generally on-line with the remainder of the needle tube so that the divergent portion resembles a small symmetrical bulge in the otherwise straight needle tube. That is, the divergent portion 40 is formed in a symmetrically arcuate configuration to ensure virtually no loss in the structural strength or integrity of the overall needle structure or the needle tip.

FIG. 4 illustrates the various orientations of the leading tip which can be made in needles according to the present invention. Advantageously, the divergent portion 40 is proportioned so that the resultant angular inclination of the leading tip portion brings the point of leading tip 34 down generally to a point on the longitudinal axis (indicated by ) of the needle tube, thereby reducing by about one-half the effective angle of the needle point to which the tissue is exposed during penetration (i.e., from an angle of about 17° to an angle of about 8 ½°) without requiring the much more expensive high strength materials. The needle point may even be brought below the center line of tube 30, as indicated at 34', down to a point where it completely shields the open interior needle chamber 32 (i.e., when it is about even with or below the heel edge 36).

Advantageously, for needles 0.045" in diameter, the length of divergent portion (as indicated at l in FIG. 4) is about ½", as measured between the points p which are generally co-linear with the lower side of the needle tube. It should be proportionately smaller for smaller diameter needles. The depth of the deviation in the needle tube (indicated at d in FIG. 4) may range from approximately ¼ to about ½ the outer diameter of the needle tube.

As shown in FIG. 3, the divergent portion (indicated at 40') can be formed by making a single, relatively small bend near the point of the needle tube. In order to ensure that the force applied to insert the needle is directly behind the point, it is preferred that the divergent portion 40' be proportioned such that the point 34 is generally within the projected cross-sectional area of the remainder of the needle tube 30. In either embodiment, the divergent portion is preferably formed without any kinking so that opposite sides of the needle tube remain approximately the same distance apart throughout the entire length of the tube, thereby avoiding any tube restriction which might otherwise interfere with full functioning of the needle assembly.

It will be understood that the divergent portion (40 or 40') can be made by any suitable device such as a forming tool which will support the tube side walls or otherwise prevent any significant kinking. The divergent portion may also be formed during the drawing operation for forming the needle tube itself, while the needle is still soft. Thus, it will be appreciated that fabrication of needles according to the present invention can be carried out as part of the fabrication of conventional needles, with no significant increase in fabrication costs and without making fabrication any more complex.

FIGS. 5A-5C illustrate the principal causes of trauma during needle penetration (the coring effect resulting from the sharp beveled edge portions at the leading edge and the shaving effect caused by the sharp heel edge with resultant jagged path) and the advance embodied in the needle according to the invention. It will be understood that the smooth surface of the needle tube, in essence, glides past the tissue once penetrated by the point of the needle tip. This is illustrated by the relatively smooth tissue lines above both needles shown in various stages of penetration in FIGS. 5A-5C.

However, during penetration of a conventional needle (indicated by "PRIOR ART NEEDLE"), the trauma is evident from the abruptly disrupted and the jagged tissue lines just below the recessed heel portion of the needle bevel, as illustrated in FIGS. 5B and 5C. In contrast, the needle of the present invention (the lowermost needle shown in each of FIGS. 5A thru 5C) generates little or no trauma, as indicated by the much smoother curvature of tissue lines below the needle. Because muscle and fat tissue are somewhat pliable and resilient and because such tissue is essentially self-lubricating, the tissue will follow the curved contour of the divergent curved segment 40 without marked tissue disruption.

In a particularly useful embodiment of the present invention, the divergent segment (40 and 40') can be formed on the needle portion of a hypodermic needle assembly for use in coronary assist procedures. As here preferably embodied, the needle portion according to the invention can simply be adapted for use as part of the coronary assist package known as Transthoracic Pacer, sold by Electro-Catheter Corporation of Rahway, N.J. As so embodied, the insertion of the needle into the heart chamber for injection of adrenaline and implantation of a helio coid pacer wire into the heart can be carried out in a relatively simple procedure.

Accordingly, the helio coid wire can already be located inside the needle tube with the curled end of the wire just behind the opening of the needle bevel while the needle actually penetrates the patient's chest and heart. There will be virtually no trauma, particularly that which would otherwise be caused by the coring effect. Thus, the need for additional structure in the form of an obturator, and the extraneous steps incident to its use, are avoided by the present invention.

It is preferred that the divergent needle portions be proportioned so that the cylindrical-like exterior surface of the leading tip be generally smooth and straight to minimize any possibility of resistance to penetration due to its angular orientation. In addition, the point of the leading tip should be located essentially within the projected cross-sectional area of the outer surface of the straight portion of the needle tube so as not to effectively enlarge the cross-sectional area of the needle tube.

It will be readily appreciated by those skilled in the art that the present invention is not limited to the specific embodiments herein shown and described. For example, the step of forming the divergent needle segment can be carried out on a non-beveled needle tube and the beveling carried out by a subsequent grinding operation. In addition, the hypodermic needle according to the present invention can be used for implantation or like procedures other than coronary assist procedures, where the coring effect in large diameter needles would otherwise have precluded the use of a needle to carry out the implantation. Thus, variations may be made within the scope and spirit of the accompanying claims, without sacrificing the principal advantages of the invention.

What is claimed is:

1. An improved needle structure for use with hypodermic needle assemblies and the like, having a generally hollow tubular needle which is beveled at one end to provide a generally truncated cylindrical leading tip segment with a relatively sharp point at its tip and which has a relatively straight portion with a straight axis therethrough, wherein the improvement comprises:
   a generally arcuate portion behind said leading tip, said arcuate portion having a generally arcuate axis which diverges from the straight axis of the needle but curves back in a direction towards the straight axis in a generally bulge-like configuration to incline said leading tip segment at a relatively small angle relative to the straight axis of the needle to shield, at least partially, its hollow interior for reducing the amount of tissue that would otherwise enter the hollow needle interior while said needle is penetrating such tissue, such that tissue trauma associated with penetration into the tissue is substantially reduced.

2. A needle according to claim 1 wherein said divergent portion is proportioned such that the point at the leading tip is generally within a cross-sectional area projected by the remainder of said needle tube by its exterior surface.

3. A needle according to claim 1 wherein said divergent portion has generally the same interior diameter throughout its entire length.

4. A needle according to claim 1 wherein said small angle is no greater than the angle formed at the beveled end of said tube.

5. A needle according to claim 1 which forms part of a coronary assist assembly, with a helio coid pacer wire located within the needle tube prior to penetration into the patient.

6. A needle according to claim 1 or 2, wherein said beveled needle end forms a heel edge recessed from but diametrically opposite said leading tip, said heel edge being located generally along a line coextensive with a straight wall portion of said tube on the side opposite said leading tip.

7. A method of forming a needle structure for hypodermic needles and the like, comprising the steps of:
   forming a generally hollow tubular needle member with a generally beveled end to provide a leading tip segment with a relatively sharp point at its leading tip; and
   forming a generally arcuate portion behind said leading tip, said arcuate portion having a generally arcuate axis which diverges from a relatively straight axis extending through another portion of said needle member but curves back in a direction towards the straight axis in a generally bulge-like configuration to incline said leading tip segment at a relatively small angle relative to the straight axis, such that said inclined leading tip segment helps prevent tissue from entering the hollow needle tube during penetration of the needle member into the tissue and reduces tissue trauma associated with penetration of the needle.

8. A method according to claim 7 wherein said divergent portion is proportioned such that the point at the leading tip is generally within a cross-sectional area projected by the remainder of said needle tube.

9. A method according to claim 7 or 8, wherein said beveled edge forms a heel edge recessed from but diametrically opposite said leading tip and wherein said heel edge is located along a line generally coextensive with a straight wall segment along a wall generally opposite said leading tip.

10. An improved coronary assist assembly which includes a hollow needle tube having a beveled face end providing a leading tip segment with a sharp point at its tip, the needle tube adapted to receive a heloi coid pacer wire within its hollow central chamber and to secure the pacer wire in a desired position within the hollow chamber and which is adapted to be coupled to a source of adrenaline or other fluid, the improvement comprising:
   a generally arcuate portion behind said leading tip, said arcuate portion having a generally arcuate axis which diverges from the straight axis of the needle but curves back in a direction towards the straight axis in a generally bulge-like configuration to incline said leading tip segment at a relatively small angle relative to the straight axis of the needle to shield, at least partially, its hollow interior for reducing the amount of tissue that would otherwise enter the hollow needle interior while said needle is penetrating such tissue, such that tissue trauma associated with penetration into the tissue is substantially reduced.

11. An improved assembly according to claim 10, wherein said beveled needle end forms a heel edge recessed from but diametrically opposite said leading tip, said heel edge being located generally along a line coextensive with a straight wall portion of said tube on the side opposite leading tip.

* * * * *